United States Patent [19]

Sorensen et al.

[11] Patent Number: 4,676,789
[45] Date of Patent: Jun. 30, 1987

[54] HEART VALVE

[76] Inventors: H. Rahbek Sorensen, Chr. Winthersvej 11, 1860 Copenhagen V, Denmark; Arne Woien, Inkognitogt 16, Postboks 7021-Homansbyen, Oslo 3, Norway

[21] Appl. No.: 734,671

[22] Filed: May 16, 1985

[51] Int. Cl.[4] .............................................. A61F 2/24
[52] U.S. Cl. ...................................................... 623/2
[58] Field of Search ........................................... 623/2

[56] References Cited

U.S. PATENT DOCUMENTS

| 4,308,624 | 1/1982 | Klawatter | 623/2 |
| 4,363,142 | 12/1982 | Meyer | 623/2 |
| 4,488,318 | 12/1984 | Kaster | 623/2 |

FOREIGN PATENT DOCUMENTS

0070259 1/1983 European Pat. Off. ................ 623/2

Primary Examiner—Richard J. Apley
Assistant Examiner—James Prizant
Attorney, Agent, or Firm—Hugh D. Jaeger

[57] ABSTRACT

Bileaflet biconical heart valve which duplicates the hemodynamics of a natural heart valve in the human heart where tips of biconical halves of the heart valve pivot outwardly in a manner representing that of natural heart valve tissue. In one embodiment of the present invention, biconical halves move about outflow pivots while in two other embodiments, the biconical halves pivot on outflow pivots where each biconical half pivots about or on two spaced pivots extending inwardly from an orifice ring at adjacent lower ends of each biconical half.

1 Claim, 21 Drawing Figures

HEART VALVE

BACKGROUND OF THE INVENTION

1. Field of the Invention

The present invention pertains to a heart valve and, more importantly, pertains to a bileaflet biconical heart valve for surgical implantation.

2. Description of the Prior Art

Prior art heart valves have attempted to mimic the natural heart valve in the hemodynamic characteristics of the natural heart valve. Most importantly, the leaflets of the prior art heart valves have attempted to duplicate the rapid closure of the natural heart valve. This has not been closely attained by the prior art heart valves.

Some prior art heart valves have made attempts to have the tips of mechanical heart valves move outwardly in a manner similar to that of natural heart valves, but have been unable to accomplish this mechanically with respect to natural tissue movement of natural heart valves. The movement of the tips of the natural heart valve regulates the hemodynamic flow of the blood, as well as other characteristics of passage of the blood through the human heart.

Finally, the prior art mechanical or tissue valves have not been provided with an oval shape which approximates some of the existing natural heart valves. This is especially important as the average heart valve in an individual is not always round, but sometimes approximates an oval geometrical cross-sectional configuration.

The present invention overcomes the disadvantages of the prior art by providing a bileaflet biconical heart valve which duplicates the natural movements of a human heart valve, and closely approximates the hemodynamic flow through the heart valve. The bileaflet biconical heart valve can be manufactured with either a circular or oval geometrical crosssection.

SUMMARY OF THE INVENTION

The general purpose of the present invention is a bileaflet biconical heart valve which provides for rapid closure of the bileaflet half portions, and approximates the hemodynamic flow of blood through the mechanical bileaflet biconical heart valve. While the bileaflet biconical heart valve is for the mitral heart valve application, the valve can be used as an aortic valve also. The bileaflet biconical heart valve can also be manufactured in an oval geometrical configuration to approximate the natural geometrical cross-sectional configuration of a heart valve in the heart.

According to one embodiment of the present invention, there is provided a bileaflet biconical heart valve with opposing symmetrical bileaflet halve portions which float about two outflow pivot pins for each bileaflet between opposing symmetrical leaflet retaining bosses and closure protrusions extending outwardly from within the orifice ring in an opposing symmetrical relationship. The leaflet retaining bosses include rotational guides, stop seats, and stop surfaces for each bileaflet.

Another embodiment of the present invention provides a bileaflet biconical heart valve including an orifice ring, opposing symmetrical outflow pivot pins supporting each biconical occluder halves on opposing pivot points at a lower portion of the biconical half within the orifice ring, a plurality of spaced opposing leaflet retaining protrusions; a plurality of leaflet stop bosses spaced about each of the biconical halves and extending outwardly within the orifice ring for closure of each of the biconical halves, and two opposing closure protrusions for extending outwardly from the interior of the orifice ring.

A further embodiment of the present invention provides a bileaflet biconical heart valve of the last embodiment where the elongated leaflet retainer protrusions are significantly reduced in size forming leaflet retainer protrusions.

One significant aspect and feature of the present invention is a bileaflet biconical heart valve which includes two biconical occluding leaflets which duplicate the natural heart valve rhythm. The heart valve includes two occluding biconical leaflets which duplicate the natural heart valve, as well as the rhythm of a natural heart valve. The tips of the biconical occluding leaflets move out in a manner like that of a natural heart valve and simulate the natural tissue of a heart valve.

Another significant aspect and feature of the present invention is a bileaflet biconical heart valve which closely approximates the hemodynamic flow of blood through a natural heart valve. This is particularly important for heart valves utilized in mitral heart valve applications.

A further significant aspect and feature of the present invention is a bileaflet biconical heart valve which can be manufactured into an oval geometrical cross-sectional configuration, which is particularly important, as natural heart valves are not always circular, but tend to approximate more closely that of an oval configuration.

Having thus described embodiments of the present invention, it is a principal object hereof to provide a bileaflet biconical heart valve.

One object of the present invention is to provide a bileaflet biconical heart valve which duplicates the natural rhythm and hemodynamic flow of a natural heart valve where the biconical halves moves in a similar fashion to natural tissue of a natural heart valve.

Another object of the present invention is to provide a bileaflet biconical heart valve where the tips of each biconical occluding leaflet movement approximates movement of tissue of a natural heart valve.

BRIEF DESCRIPTION OF THE DRAWINGS

Other objects and many of the attendant advantages of the present invention will be readily appreciated as the same becomes better understood by reference to the following detailed descriptions when considered in connection with the accompanying drawings, in which like reference numerals designate like parts throughout the figures thereof and wherein.

DESCRIPTION OF THE PREFERRED EMBODIMENTS

Figure 1:
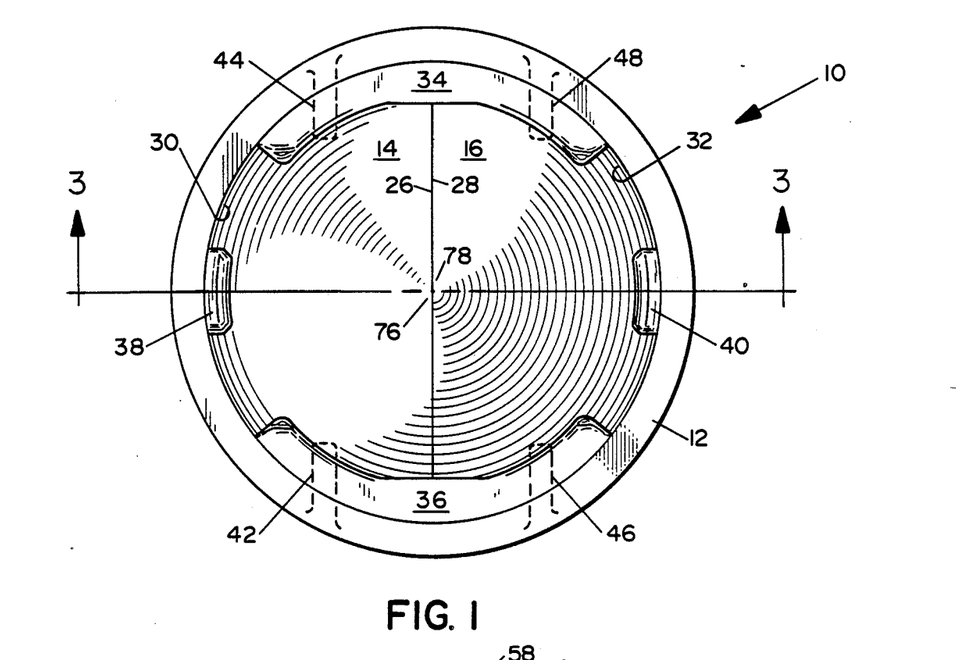
FIG. 1 illustrates a top view of a bileaflet biconical heart valve of the present invention.
Figure 2:
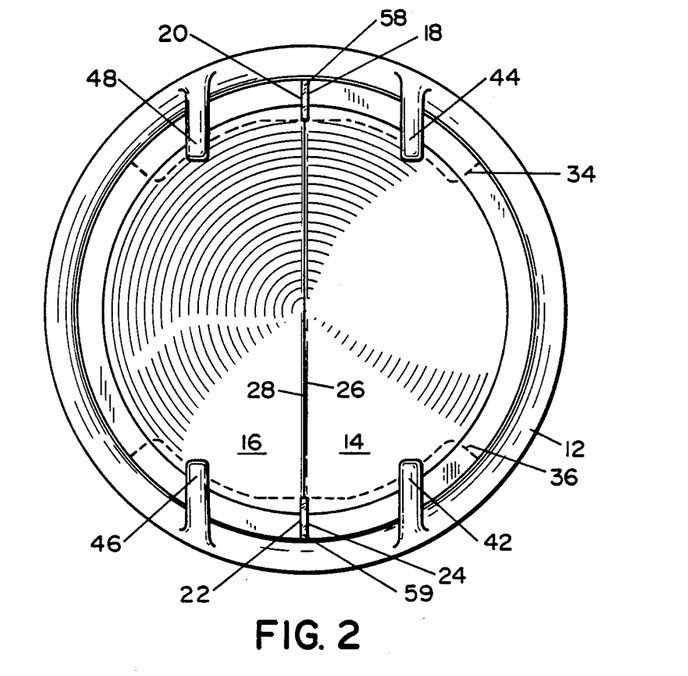
FIG. 2 illustrates a bottom view.
Figure 3:
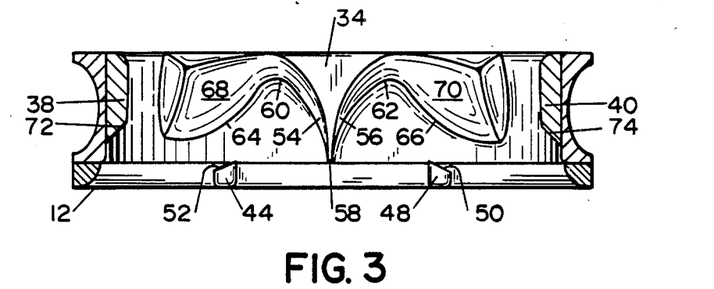
FIG. 3 illustrates a view taken along line 3—3, excluding leaflet halves, of FIG. 1.

FIG. 1, which illustrates a top view of a bileaflet biconical heart valve 10, the present invention, shows the biconical heart valve 10 including a valve housing orifice ring 12, and biconical occluding leaflet halves 14 and 16, including chamfered machined leaflet valve corners 18, 20, 22 and 24 as shown in FIG. 2, for closing occluding leaflet halves 14 and 16 which include closure surfaces 26 and 28 and round beveled closure surfaces 30 and 32. Leaflet retaining bosses 34 and 36 align on opposing ends of the closure access of the valve and extend inwardly from opposing upper, mid, and lower portions of the orifice ring 12. Closure protrusions 38 and 40 determine the closure access of the leaflets 14 and 16 and extend inwardly from opposing mid portions of the orifice ring 12. The leaflet retaining bosses 34 and 36 and leaflet closure protrusions 38 and 40, symmetrically extend inwardly from the orifice ring 12 as also illustrated in FIG. 3. Corresponding and opposing outflow pivot pins 42 and 44 and 46 and 48, illustrated in hidden lines, extend inwardly from a lower portion of the orifice ring 12, providing for pivoting of the leaflets during movement of the biconical occluding leaflet halves 14 and 16 which ride on each of the partially rounded pivot pins 42, 44, 46, and 48.

FIG. 2 illustrates a bottom view of the biconical heart valve 10 of FIG. 1 wherein the valve has been rotated about its pictorial vertical axis, and where all numerals correspond to those elements previously described. Shown in particular, in hidden lines, are leaflet retaining bosses 34 and 36. Opposing leaflet retaining boss center members 58 and 59 are also illustrated, which are later described in detail.

FIG. 3 illustrates a view taken along line 3-3, excluding leaflet halves 14 and 16 of FIG. 1 where all numerals correspond to those elements previously described. The outflow pivots 44 and 48 include flat portions 52 and 50. The leaflet retaining boss 34 includes symmetrical opposing rotational guides 54 and 56, center member 58, stop seats 60 and 62, and small stop surfaces 64 and 66, as well as large stop surfaces 68 and 70. Like associated elements on the like opposing side of the heart valve 10 are not numbered for purpose of brevity in the specification and drawing. The closure protrusions 38 and 40 include closure protrusion surfaces 72 and 74, respectively.

Figure 4:
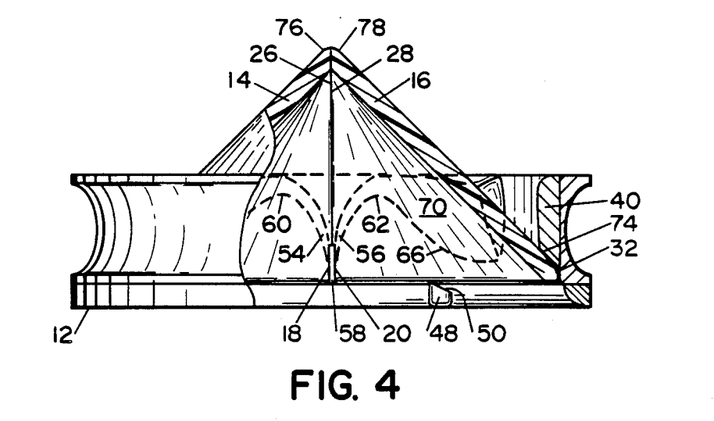
FIG. 4 illustrates a side view partially in crosssection with biconical occluding leaflet halves closed.

FIG. 4 illustrates a side view, partially in section, showing the biconical leaflet halves 14 and 16 in a closed position, as illustrated in FIGS. 1 and 2. All numerals correspond to those elements previously described. Tips 76 and 78 of each of the leaflets are illustrated.

Figure 5:
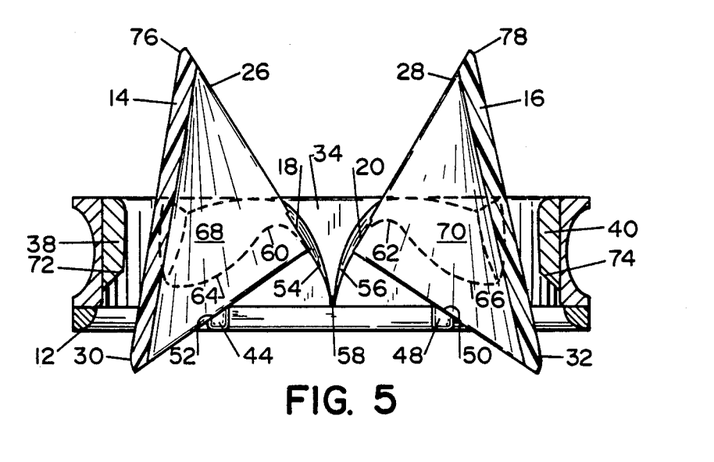
FIG. 5 illustrates a view in cross-section with the biconical halves open.

FIG. 5 illustrates a side view in section of the biconical leaflet halves 14 and 16 in an open position, providing for the passage of blood in a hemodynamic flow which approximates that of a natural valve. All numerals correspond to those previously described.

Figure 6:
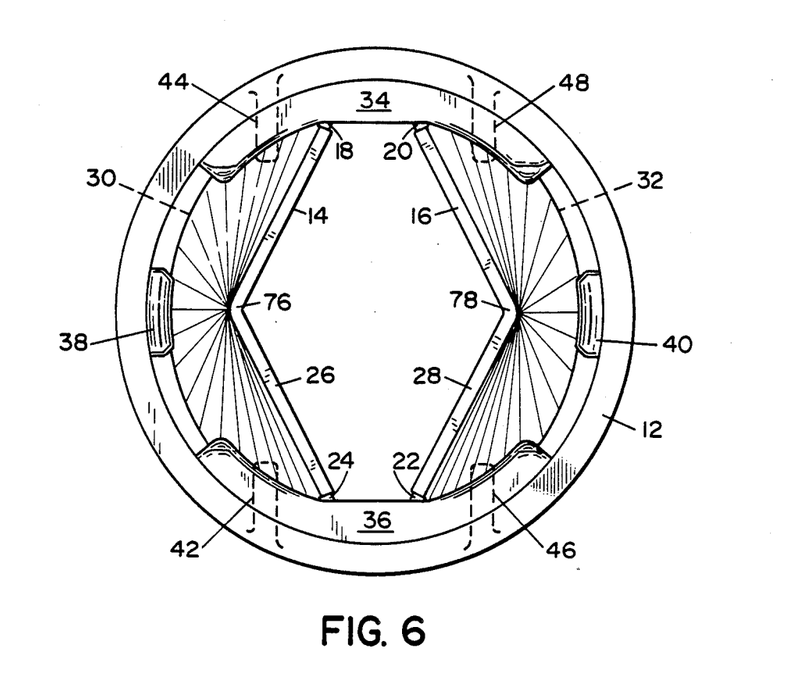
FIG. 6 illustrates a top view with the biconical halves open.

FIG. 6 illustrates a top view, in full, of FIG. 5. All numerals correspond to those previously described. The position of tips 76 and 78 are noted. The opening resembles a modified hexagon cross-section.

Figure 7:
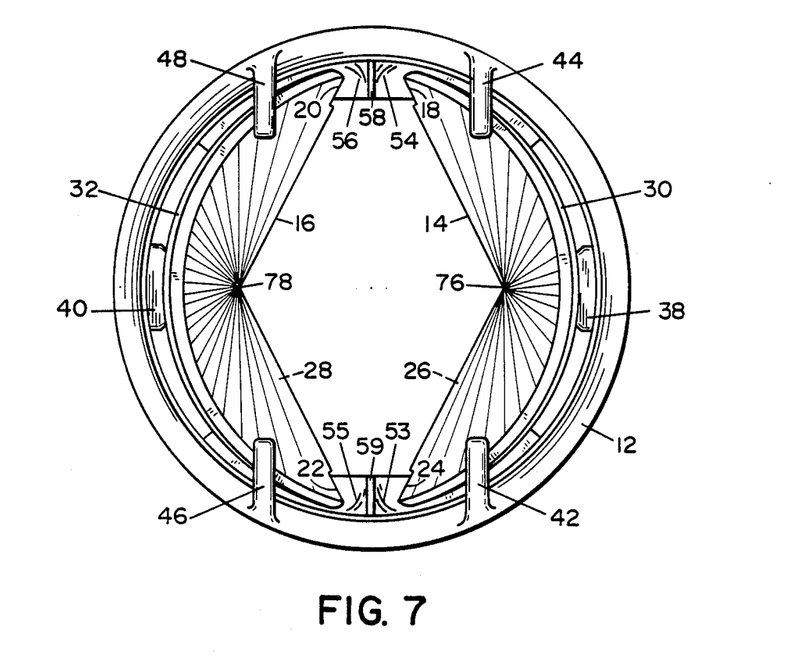
FIG. 7 illustrates a bottom view with the biconical halves open.

FIG. 7 illustrates a bottom view of FIG. 6 where all numerals correspond to those elements previously described.

MODE OF OPERATION

The heart valve 10 of the present invention can be manufactured in a plurality of sized diameters. The particular size of the heart valve is determined by the sewing ring, not illustrated, around the outer diameter of the orifice ring 12. Sewing rings are known in the prior art which usually are a knitted teflon ring. Prior to implant, a surgeon will size the diameter of the tissue orifice, such as through the use of heart valve sizers which are also known in the prior art. Once a diameter of the heart valve implant is determined, the appropriate diameter heart valve can be selected from surgical supply stock accordingly. The diameter of the mitral or aortic valves will vary, of course, from one individual to another individual, and of course being dependent upon an adult male, an adult female, or a small child.

The orifice ring 12 can be manufactured from a suitable material, such as titanium or stainless steel. The bileaflets 16 and 14 can be manufactured from Pyrolite carbon. These materials are currently used in heart valves and approved for use by the FDA. The materials are light weight and radiopaque, which are particularly lended to these types of applications. The orifice ring 12, including the leaflet retaining bosses 34 and 36, the closure protrusions 38 and 40, and the pivots 42–48 can all be manufactured from a single metallic unit, such as by computer machining the orifice ring and components from a single piece of titanium, for example.

In describing the mode of operation of the bileaflet biconical heart valve 10, as illustrated in FIGS. 1–7, movement of the leaflets 14 and 16 are identical with respect to each other about the pivots 42–48. FIGS. 1, 2, and 4 illustrate the leaflets 14 and 16 in a closed position at rest, resting on the pivots 42–48, which are aligned against the leaflet retaining boss center members 58 and 59. Each of the leaflets 14 and 16 are in a free floating, non-binding position with respect to the internal wall of the orifice ring 12 and provide for mating of the closure surfaces 26 and 28 in a closed position. The leaflets rest against the surfaces 72 and 74 of the closure protrusions 38 and 40 in a rest position, as well as against the center members 58 and 59, and on the pivots 42-48.

The leaflets 14 and 16 pivot based on pressure differentials during blood flow. Each of the leaflets 14 and 16 move between a closed position of FIGS. 1, 2 and 4 to an open position of FIGS. 5-7. The leaflet retaining bosses 34 and 36 maintain the leaflets within the orifice ring during pivoting movement, and provide for movement of each of the leaflets conforming to the aligned surfaces of the leaflet retaining bosses 34 and 36. The leaflets move in such a manner that the tips 76 and 78 of each of the leaflets can be described as an arcuate movement path. FIG. 5 best illustrates the leaflets 14 and 16 in a fully open position where the leaflets have moved over and about the pivots 44 and 46, and rest on the flat portions of 50 and 52 of the pivots in a fully opened position. The pressure differential between the proximal side and distal side of the heart valve provides for the pivoting action of each of the leaflets, based on the flow of the blood. The pivoting of the leaflet is provided by the rotational guides 54 and 56, as illustrated in FIG. 3, for which the edges 18 and 20 of each leaflet pivots about and the leaflet subsequently comes to a fully opened position against stop surfaces 64 and 66, as well as 68 and 70 of bosses 34 and 36. FIGS. 6 and 7 illustrates the leaflets 14 and 16 in a fully opened position providing for free flow of optimized volume of blood through the central orifice created by the tips 76 and 78 of the respect leaflets. The outward bound shape of the valve in a fully opened position resembles a slightly elongated hexagonal opening providing for minimum blood flow turbulence during the flow of blood through the valve 12.

The closure of the heart valve 10 is accounted for by a decrease in pressure on the proximal side with respect to the distal side in that blood flows back through the valve orifice. As a consequence, the reverse flow pivots the leaflets downwardly to a position as illustrated in FIG. 1, 2, and 4. The free floating leaflets respond quickly to reverse blood flow through the valve providing rapid closure. The closure between the surfaces 26 and 28 is so minimal as to provide for a negligible, if any, leakage of blood when the leaflets are closed.

SECOND EMBODIMENT

Figure 8:
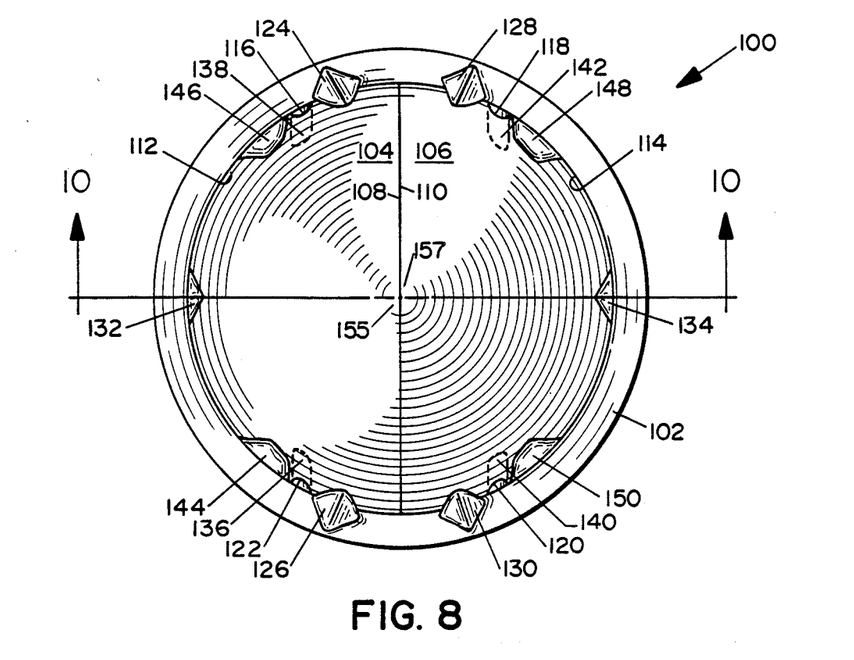
FIG. 8 illustrates a second embodiment of the present invention of a top view of a bileaflet biconical heart valve.

FIG. 8, which illustrates a top view of bileaflet biconical heart valve 100, the present invention, shows the heart valve 100 including a valve housing orifice ring 102 and biconical occluding leaflet halves 104 and 106 as later described. Leaflet halves 104 and 106 include closure surfaces 108 and 110, round beveled closure surfaces 112 and 114, and pivot slots 116, 122, 118, and 120, respectively. Opposing aligned leaflet stp bosses 124 and 126 and 128 and 130, symmetrically align on opposing interior upper portions of the orifice ring 102. Closure protrusions 132 and 134 extend inwardly from the mid portion of orifice ring 102 and determine the closure of the leaflets 104 and 106, respectively. The leaflet stop bosses 124-130 and leaflet closure protrusions 132 and 134 extend inwardly from the orifice ring 102. Corresponding and opposing outflow pivots 136 and 138 and 140 and 142, illustrated in hidden lines, extend inwardly in a lower portion of ring 102, as illustrated, providing for pivoting of the leaflets 104 and 106 on pivots 136-142 during movement of the biconical leaflet occluding halves 104 and 106. Elongated leaflet retainer protrusions 144, 146, 148 and 150 extend inwardly from a mid portion of the orifice ring 102 enhancing rotational engagement of biconical occluding leaflet halves 104 and 106 about the outflow pivots 136-142.

Figure 9:
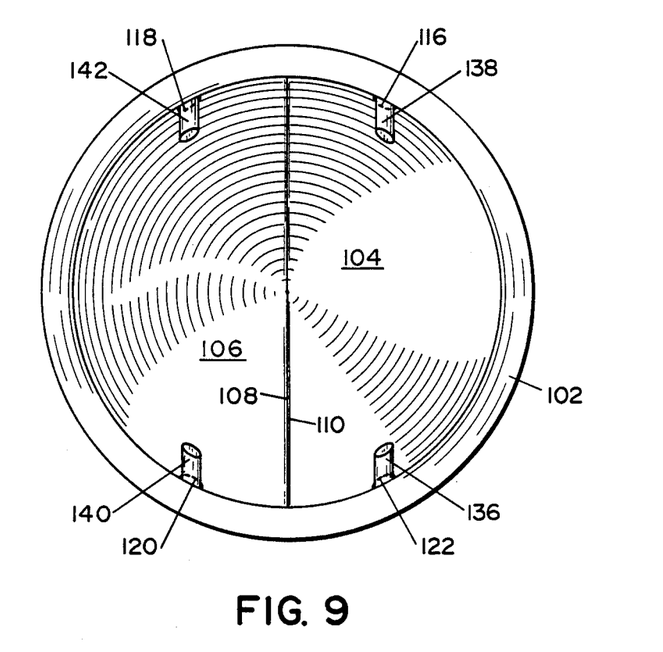
FIG. 9 illustrates a bottom view.

FIG. 9 illustrates a bottom view of the biconical heart valve 100 f FIG. 8 wherein the valve has been rotated about its pictorial vertical axis. All numerals correspond to those elements previously described.

Figure 10:
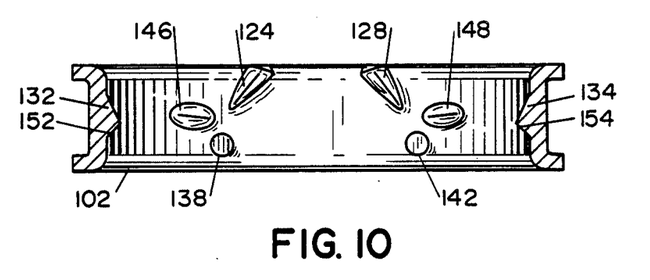
FIG. 10 illustrates a view taken along line 10—10, excluding leaflet halves, of FIG. 8.

FIG. 10 illustrates a section view taken along line 10—10, excluding leaflet halves 104 and 106, of FIG. 8 where the numerals correspond to those elements previously described. The outflow pivots 138 and 142, stop bosses 124 and 128 and elongated leaf retainer protrusions 146 and 148 extend inwardly from orifice ring 102. The closure protrusions 132 and 134 include closure protrusion surfaces 152 and 154, respectively.

Figure 11:
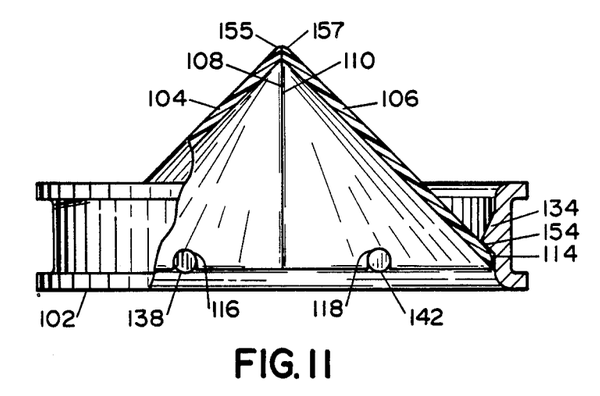
FIG. 11 illustrates a side view partially in cross-section with biconical occluding leaflets halves closed.

FIG. 11 illustrates a side view, partially in section, showing the biconical leaflet halves 104 and 106 in a closed position, as previously illustrated in FIGS. 8 and 9. All numerals correspond to those elements previously described. Tips 155 and 157 of each of the leaflets are illustrated.

Figure 12:
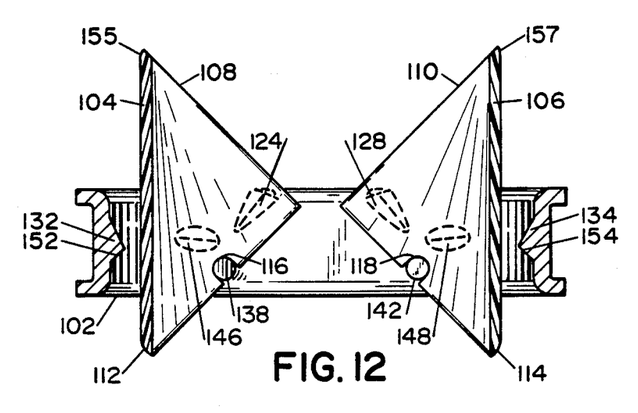
FIG. 12 illustrates a view in cross-section with the biconical halves open.

FIG. 12 illustrates a side view in section of the biconical leaflet halves 104 and 106 in an open position, roviding for the passage of blood in a hemodynamic flow which approximates that of a natural heart valve. All numerals correspond to those elements previously described.

Figure 13:
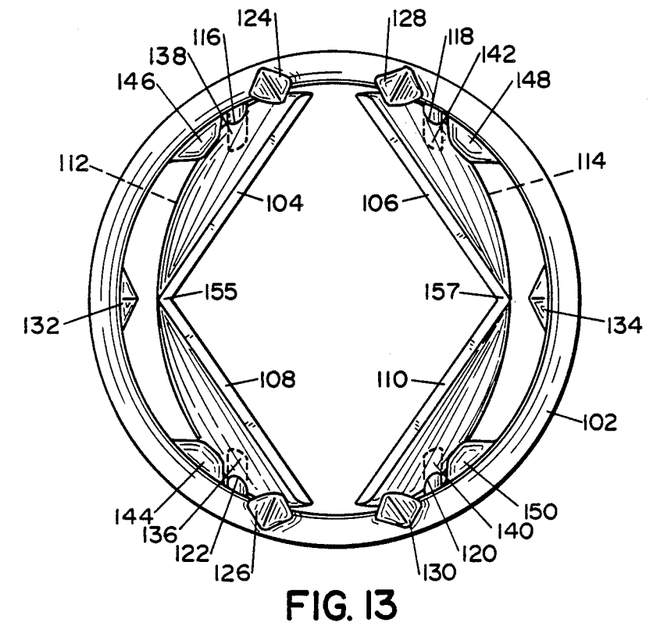
FIG. 13 illustrates a top view with the biconical halves open.

FIG. 13 illustrates a top view, in full, of FIG. 12. All numerals correspond to those previously described. The occluding leaflets are in an open position.

Figure 14:
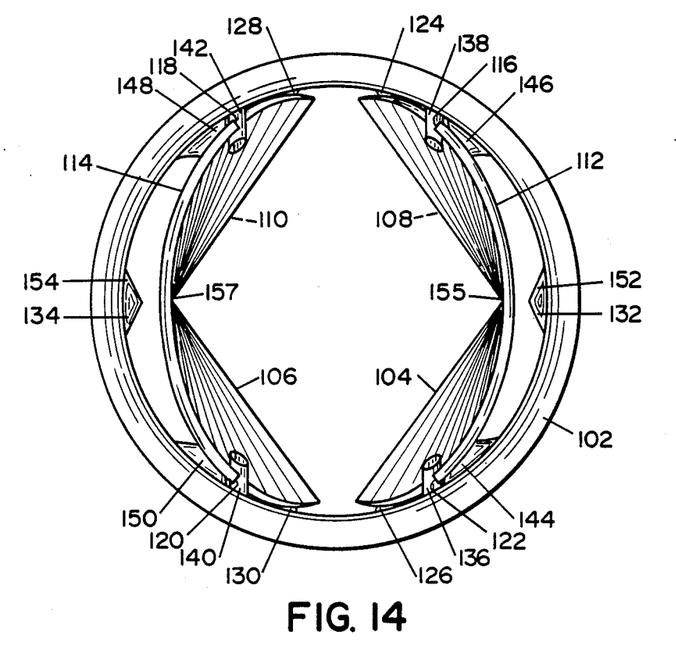
FIG. 14 illustrates a bottom view with the biconical halves open.

FIG. 14 illustrates a bottom view of FIG. 13 where all numerals correspond to those elements previously described.

MODE OF OPERATION OF SECOND EMBODIMENT

The operation of the heart valve 100 of FIGS. 8-14 is similar in theory to that of FIGS. 1-7; although, the structure of the heart valve 100 is slightly different. The leaflets 104 and 106, pivot on pivots 136-142 in pivot slots 116-122 in lieu of FIGS. 1-7 where the leaflets 14 and 16 pivot about the pivots 42-48. In FIGS. 8-14, the leaflets are actually hinged on the pivots as best illustrated in FIG. 12, illustrating pivot slots 116 and 118 in each of the leaflets 104 and 106, for pivoting about the pivots 138 and 142 in a rotational manner. Pivoting of each of the leaflets in a rotational manner is controlled by the elongated leaflet retainer protrusions 144-150. In a fully opened position, the leaflets will stop against the stop bosses 124-130, while in a closed position the leaflets will rest against closure protrusion surfaces 152 and 154 of closure protrusions 132 and 134. FIGS. 8, 9, and 11 illustrate the heart valve in a closed position, while FIGS. 12-14 illustrate the heart valve in an open position.

THIRD EMBODIMENT

Figure 15:
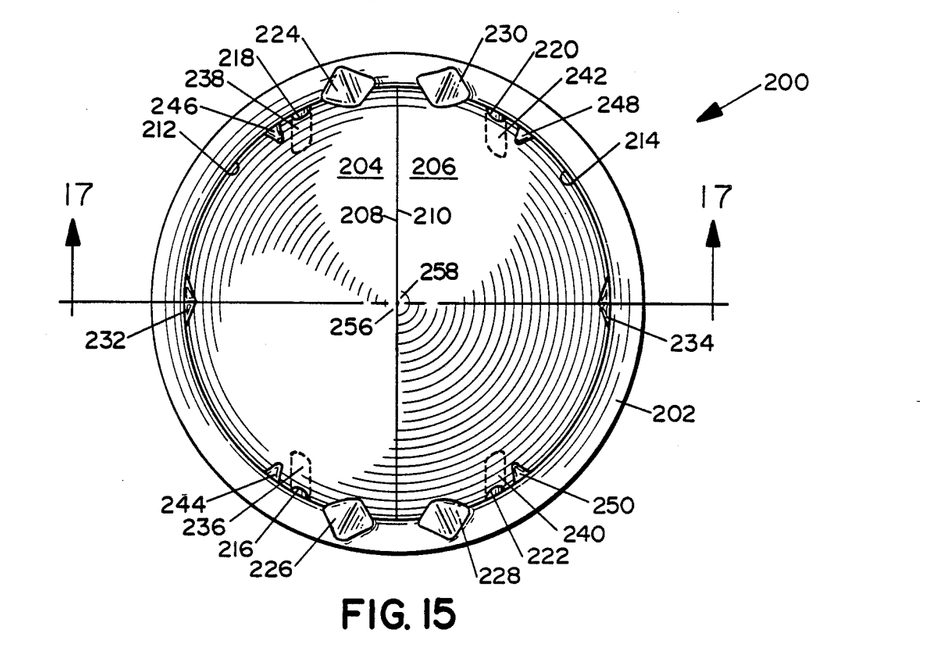
FIG. 15 illustrates a third embodiment of the present invention of a top view of a bileaflet biconical heart valve.

FIG. 15, which illustrates a top view of the bileaflet biconical heart valve 200, the present invention, shows the heart valve 200 including a valve housing orifice ring 202 and biconical occluding leaflet halves 204 and 206 as later described. Leaflet halves 204 and 206 include closure surfaces 208 and 210, round beveled closure surfaces 212 and 214, and pivot slots 216, 218, 220, and 222. Opposing aligned leaflet stop bosses 224 and 226 and 228 and 230 symmetrically align on opposing interior upper portions of the orifice ring 202. Closure protrusions 232 and 234 extend inwardly from the mid portion of orifice ring 202 determining the closure of the leaflets 204 and 206, respectively. The leaflet stop bosses 224-230 and leaflet closure protrusions 232 and 234 extend inwardly from the orifice ring 202. Corresponding and opposing outflow pivots 236 and 238 and 240 and 242, illustrated in hidden lines, extend inwardly from the lower portion of the orifice ring 202 as illustrated, providing for pivoting of the leaflets 204 and 206 during movement of the biconical leaflet occluding halves 204 and 206. Conical like leaflet retainer protrusions 244, 246, 248 and 250 extend inwardly from orifice ring 202 to ensure engagement of biconical leaflet halves 204 and 206 upon outflow pivots 236-242.

Figure 16:
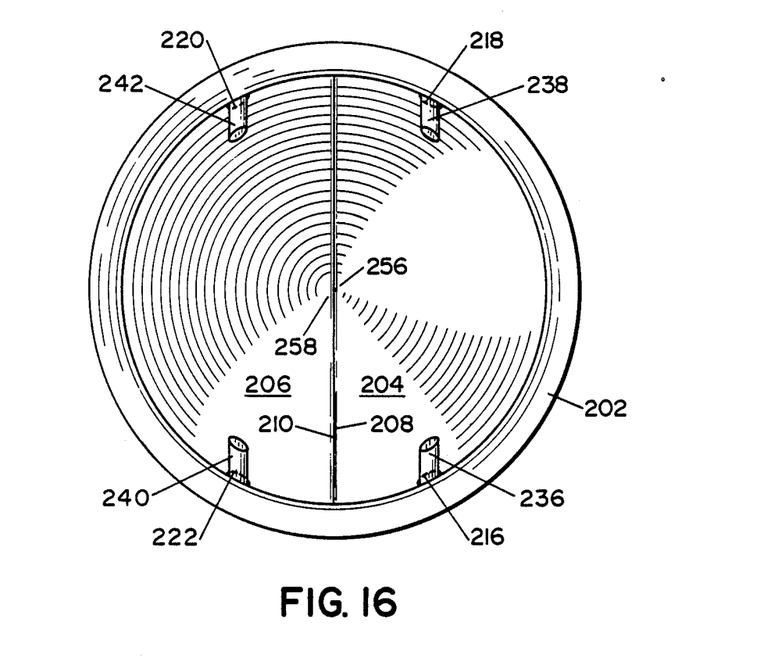
FIG. 16 illustrates a bottom view.

FIG. 16 illustrates a bottom view of the biconical heart valve 200 of FIG. 15 wherein the valve has been rotated about its pictorial vertical axis. All numerals correspond to those elements previously described.

Figure 17:
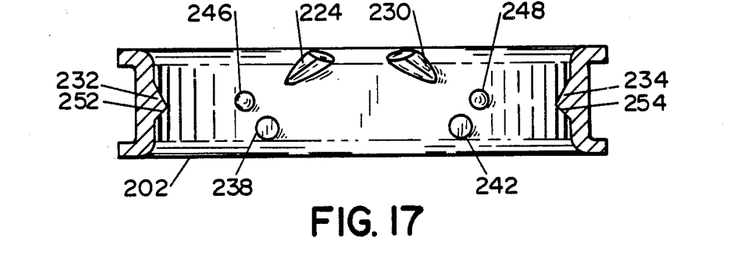
FIG. 17 illustrates a view taken along line 17—17, excluding leaflet halves, of FIG. 15.

FIG. 17 illustrates a sectinal view taken along line 17—17, excluding leaflet halves 204 and 206, of FIG. 15 where the numerals correspond to those elements previously described. The outflow pivots 238 and 242, stop bosses 224 and 230, and conical leaf retainer protrusions 246 and 248 extend inwardly from orifice ring 202. The closure protrusions 232 and 234 include closure protrusion surfaces 252 and 254, respectively.

Figure 18:
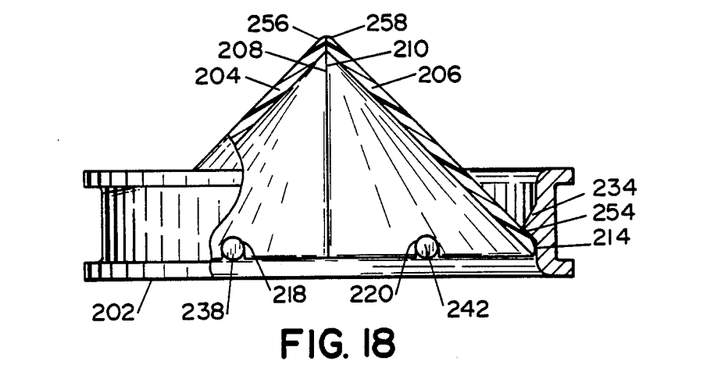
FIG. 18 illustrates a side view partially in cross-section with biconical occluding leaflet halves closed.

FIG. 18 illustrates a side view, partially in section, showing the biconical leaflet halves 204 and 206 in a closed position, as previously illustrated in FIGS. 15 and 16. All numerals correspond to those elements previously described.

Figure 19:
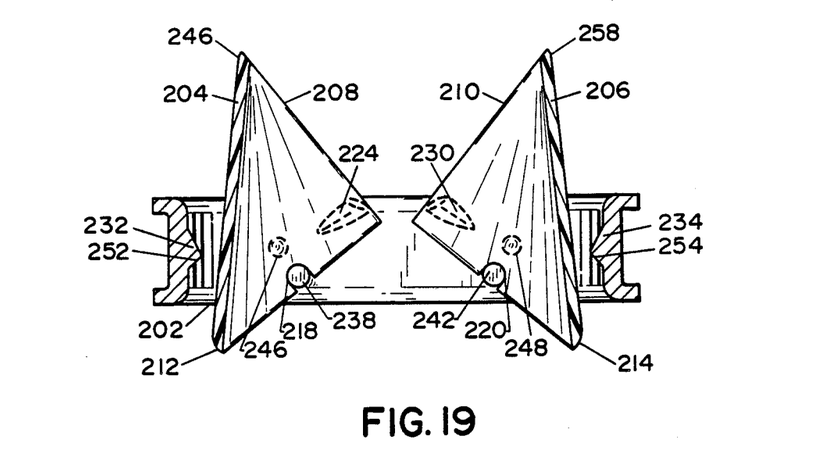
FIG. 19 illustrates a view in cross-section with the biconical halves open.

FIG. 19 illustrates a side view in section of the biconical leaflet halves 204 and 206 in an open position, providing for the passage of blood in a hemodynamic flow which approximates that of a natural heart valve. All numerals correspond to those elements previously described.

Figure 20:
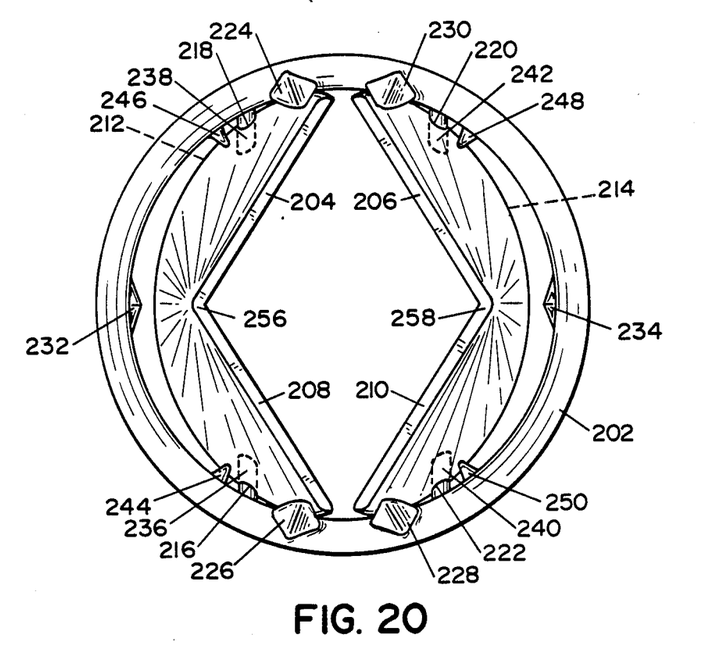
FIG. 20 illustrates a top view with the biconical halves open.

FIG. 20 illustrates a top view, in full, of FIG. 19. All numerals correspond to those previously described. The occluding leaflets are in an open position.

Figure 21:
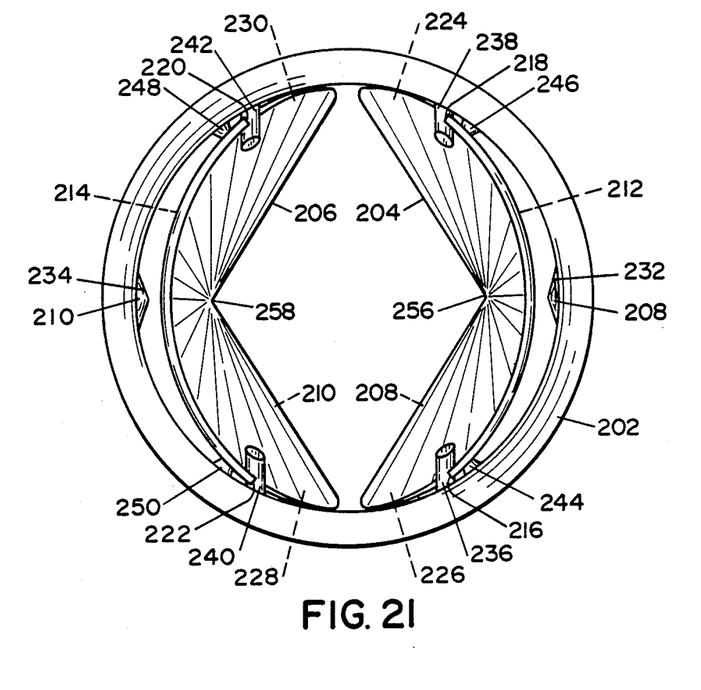
FIG. 21 illustrates a bottom view with the biconical halves open.

FIG. 21 illustrates a bottom view of FIG. 20 where all numerals correspond to those elements previously described.

MODE OF OPERATION OF THIRD EMBODIMENT

FIGS. 15-21 are identical in operation to that of FIGS. 8-14. The particular main difference between the structure is that the leaflet retainer protrusions 244-250 are conical in shape and are considerably smaller than the elongated retainer protrusions of FIGS. 8-14. Also, the leaflet stop bosses 224-230 are somewhat smaller than the leaflet stop bosses of FIGS. 8-14. Also, leaflet closure protrusions 232 and 234 are considerably small than the closure protrusions of FIGS. 8-14. Otherwise, the structure of the valve is similar to that, not only in structure but in operation, to that of FIGS. 8-14. For purposes of brevity, the mode of operation should be referred to for FIGS. 8-14 with respect to the second embodiment of FIGS. 15-21.

We claim:
1. Heart valve comprising:
 a. orifice ring;
 b. opposing pairs of symmetrically spaced pivots extending inwardly from a lower portion of said orifice ring, said pivots lying on a plane substantially perpendicularly to the axis of said orifice ring;
 c. opposing pairs of symmetrically spaced inwardly extending conical leaflet retainer protrusions from a mid portion of said orifice ring;
 d. opposing pairs of symmetrically spaced inwardly extending elongated leaflet stops extending from an upper portion of said orifice ring;
 e. opposing pairs of symmetrically spaced closure protrusions extending inwardly from a mid portion of said interior of said orifice ring, and;
 f. two biconical occluding leaflets for substantially horizontal rotational movement around said pivots, each of said leaflets including pivot slots for accepting said pivots, said leflets also pivoting about said leaflet retainer protrusions and between said closure protrusions in a closed occluding position and to said leaflet stop in a non-occluding open position.

* * * * *